United States Patent [19]

Barabas et al.

[11] 4,312,995
[45] Jan. 26, 1982

[54] COPOLYMERIZABLE ULTRAVIOLET LIGHT ABSORBER MEMBERS WHICH ARE $\alpha,\beta$-UNSATURATED DICARBOXYLIC ACID HALF-ESTERS OF 2-HYDROXY,ALKOXY,METHYLOLBENZOPHENONES

[75] Inventors: Eugene S. Barabas, Watchung; Prakash Mallya, Bloomingdale; Stanley J. Gromelski, Jr., W. Caldwell, all of N.J.

[73] Assignee: GAF Corporation, New York, N.Y.

[21] Appl. No.: 168,224

[22] Filed: Jul. 10, 1980

[51] Int. Cl.³ .................................................. C07C 59/84
[52] U.S. Cl. .................................. 560/194; 526/313; 526/316
[58] Field of Search .............. 560/194; 260/45.85 P; 526/313, 316

[56] References Cited

U.S. PATENT DOCUMENTS

| | | | |
|---|---|---|---|
| 2,967,186 | 1/1961 | Gordon et al. | 260/348 |
| 3,322,817 | 5/1967 | Goldberg et al. | 560/85 |
| 3,704,255 | 11/1972 | Braun | 560/85 X |
| 4,177,122 | 12/1979 | Sato | 560/209 X |
| 4,186,151 | 1/1980 | Kubota et al. | 568/333 X |

Primary Examiner—Natalie Trousof
Assistant Examiner—Vera C. Clarke
Attorney, Agent, or Firm—James Magee, Jr.; Walter Katz

[57] ABSTRACT

This invention relates to copolymerizable ultraviolet light absorber monomers which are $\alpha,\beta$-unsaturated dicarboxylic half-esters of 2-hydroxy,alkoxy,methylolbenzophenone intermediate compounds. The monomers have the formula:

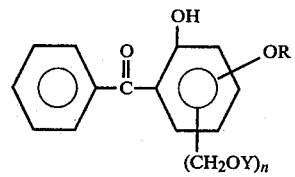

where R is alkyl $C_1$–$C_8$, and
n is 1 or 2, and
Y is a half-acyl radical of a $\alpha,\beta$-unsaturated dicarboxylic acid selected from the group of maleic and itaconic acids.

The monomers herein are made by monoesterifying intermediate compounds, prepared by converting a 2-hydroxy,alkoxy,benzophenone to the corresponding methylol derivative by a formylation reaction, with the anhydride of the desired acid.

In the preferred embodiments of the invention, the alkoxy group is methoxy in the 4-position, the methylol group which is half-esterified is a monomethylol group located at the 3- or 5- position of the phenyl ring containing the hydroxy group, and the acid anhydride is maleic anhydride.

Copolymerization of the monomers herein with vinyl monomers provide improved ultraviolet light stable copolymers for industrial and commercial applications.

11 Claims, No Drawings

COPOLYMERIZABLE ULTRAVIOLET LIGHT ABSORBER MEMBERS WHICH ARE α,β-UNSATURATED DICARBOXYLIC ACID HALF-ESTERS OF 2-HYDROXY,ALKOXY,METHYLOLBENZOPHENONES

BACKGROUND OF THE INVENTION

1. Field of the Invention

This invention relates to copolymerizable light absorber monomers and, more particularly, to α,β-unsaturated dicarboxylic acid half-esters of 2-hydroxy,alkoxy,methylolbenzophenes, which can copolymerize with various unsaturated monomers to provide copolymer materials having improved resistance to degradation by light.

2. Description of the Prior Art

Various organic compounds exhibit the power to absorb electromagnetic radiation and can be incorporated in various plastic materials such as transparent sheets which act as filters for all the radiation passing through and will transmit only such radiations as are not absorbed by the sheet and/or the absorbing agent. Such filters find use in many technical and commercial applications.

Numerous acrylic compounds have been suggested as absorbents for the range of radiations described above. For specific compounds, see U.S. Pat. Nos. 3,081,280; 3,272,810; 3,644,466; 3,256,312 and 3,215,724. These ultraviolet absorbers are mechanically mixed with the plastic materials to prevent discoloration and degradation of the material. However, it has been observed that such absorbers sometimes fail or are blocked out of the plastic under adverse weather conditions before the lifetime of the protected material. Also, it is not possible to use all of these ultraviolet absorbers with radiation curing of the plastic material. Another disadvantage of these ultraviolet absorbers is the high amount of absorber needed for protection of some materials.

Hydroxy,alkoxybenzophenone compounds are known to be effective ultraviolet light absorbers and stabilizers. For example, in U.S. Pat. No. 4,186,151, there is disclosed in detail literature and patent references relating to such compounds and derivatives thereof. Additionally, in U.S. Pat. No. 4,177,122 there is described the preparation of ultraviolet light sensitive compounds obtained by reacting a hydroxybenzophenone with an alkylene oxide and esterifying with an unsaturated end group, which are useful particularly in making printing inks.

CROSS-REFERENCE TO RELATED APPLICATIONS

FDN-1259/B, Ser. No. 168,223, filed 7/10/1980 by the same inventors and assigned to the same assignee as herein, describes and claims related copolymerizable ultraviolet light acrylic ester absorber absorber monomers.

FDN-1259/A, Ser. No. 153,107, filed 5/23/1980 by the same inventors and assigned to the same assignee as herein, describes and claims the intermediate methylol compounds used herein.

SUMMARY OF THE INVENTION

In accordance with the invention, there is provided herein copolymerizable ultraviolet light absorber monomers, which are α,β-unsaturated dicarboxylic acid half-esters of 2-hydroxy,alkoxy,methylolbenzophenones, said compounds having the formula:

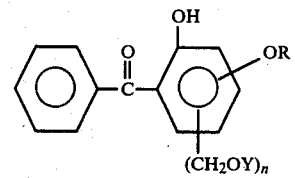

where R is alkyl $C_1$–$C_8$, and
n is 1 or 2, and
Y is a half-acyl radical of an α,β-dicarboxylic acid selected from maleic and itaconic acids.

In the preferred embodiments of the invention, the —OR group is methoxy in the 4-position, —$CH_2OY$ is located at the 3- or 5- positions of the phenyl ring, Y is derived from maleic acid, and n is 1.

DETAILED DESCRIPTION OF THE INVENTION

The intermediate compounds used in the invention are made by formylation of a 2-hydroxy,alkoxybenzophene starting material having the formula:

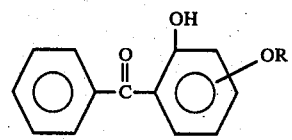

where R is alkyl $C_1$–$C_8$,
with formaldehyde in aqueous alkaline solution at a pH of about 12–13, and at a temperature of less than 40° C., preferably at room temperature, using a water-miscible organic solvent to keep the benzophenone in solution.

An alkyl group is defined herein as being either straight chain or branched, including methyl, ethyl, propyl, butyl, octyl, isopropyl, isobutyl and the like.

During the formylation reaction, an excess of formaldehyde in the reaction mixture prevents side reactions from occurring, thus increasing the yield of the desired methylol product. Accordingly, when the molar ratio of benzophenone to formaldehyde is adjusted to 1:1, a yield of about 70% of predominately the 5-monomethylol intermediate is obtained during a 24-hour reaction period. On the other hand, by using a ratio with an excess of formaldehyde, e.g., about 1:3, the yield of methylol compounds is about 95%. The product is a mixture of the 5- and 3- monomethylol compounds, in about a 60:40 ratio of each, and some 3,5-dimethylol compound, during a 5½ hour reaction period. Still higher ratios may be used, too, but the substantial excess of formaldehyde must be separated from the reaction products, which is undesirable.

The concentration of the reactants is not critical. Generally they are made low enough to keep them in solution but sufficiently high to enable the reaction to proceed at a reasonable reaction rate. Usually the benzophenone is present at a concentration of about 30% by weight, and the formaldehyde about 10% by weight of the solution. The alkali is present at a concentration of about 10%.

After the methylol intermediate is formed, the reaction product mixture is acidified and washed with water. Then unreacted formaldehyde, which is present in the organic phase, is removed under vacuum. The resultant oily organic product is dried overnight over molecular sieves to remove residual traces of water.

The intermediate product may be isolated as an individual compound or compounds, or kept as a mixture of several compounds. Either form may be immediately converted to the desired copolymerizable ultraviolet light absorber compounds by monoesterification with an $\alpha,\beta$-unsaturated carboxylic acid anhydride, itaconic anhydride and citraconic anhydride and the like.

The presence of the primary methylol group on the phenyl ring of the benzophenone intermediate enables the preparation of monoesters of these unsaturated acids with relative ease. The monomers of the invention are characterized by nuclear magnetic resonance ($^1$H, $^{13}$C) and ultraviolet spectroscopy.

The copolymerizable ultraviolet light absorber monomers then are copolymerized with unsaturated monomers, generally by emulsion, suspension or solution polymerization, to provide copolymer materials having ultraviolet absorber protection built into the molecule. Suitable monomers for this purpose include styrene, butadiene, and their mixtures, vinyl pyrrolidone, and the like.

The following non-limiting examples will illustrate the invention more particularly.

EXAMPLE 1

Preparation of
2-Hydroxy,alkoxy,methylolbenzophenone Maleate Half-Ester

A. 2-Hydroxy,alkoxy,methylolbenzophenone

Into a 100 ml. 3-necked flask equipped with thermometer, dropping funnel and magnetic stirrer is charged 2-hydroxy-4-methoxybenzophenone (65.2 g., 0.286 moles) dissolved in 11.44 g. of sodium hydroxide in 115 g. of distilled water, and 64 ml. of tetrahydrofuran is added to produce a clear solution. The 27% solution of formaldehyde (64.0 g., 0.789 moles) is added with stirring at room temperature and the reaction is allowed to proceed for 5½ hours. Thereafter the reaction product mixture is acidified to a pH of 5–6, using a 50% acetic acid solution, and washed several times with distilled water. Then the unreacted formaldehyde present in the organic phase is removed by rotating the mixture on a Rotovac in vacuum. The organic phase is dried overnight over molecular sieves. The yield is 60.0 g. of a mixture of the desired intermediate products which may be used as such for the subsequent esterification reaction with the unsaturated anhydride or acid halide. The 5-methylol intermediate is about 58 parts, the 3-methylol intermediate about 38 parts and the 3,5-dimethylol intermediate about 4 parts of the mixture.

B. The reaction product of A (40 g.,) is dissolved in a solution of maleic anhydride (15.4 g., 0.157 moles) in 25 ml. of anhydrous methylethylketone. The resulting solution then is heated to 35° C., and held there for 10 hours, whereupon 25 ml. of methyl butyl ketone is added. The solution is washed with water, dilute sodium carbonate solution again several times with water, and finally the desired monomer product is dried over molecular sieves.

EXAMPLE 2

Preparation of
2-Hydroxy-4-Alkoxy-5-Methylolbenzophenone Maleate Half-Ester

The procedure of Example 1A is repeated using 2-hydroxy-4-methoxybenzophenone (65.2 g., 0.286 moles) and 37% formaldehyde (23.2 g., 0.286 moles), for 24 hours. The methylol product is predominately the 5-methylol intermediate, 55.4 g., obtained in a yield of 75%. The procedure of Example 1B then is repeated to provide the desired monomer.

EXAMPLE 3

Preparation of
2-Hydroxy,alkoxy,methylolbenzophenone Itaconate Half-Ester

The procedure of Example 1 is repeated with itaconate anhydride to provide the desired monomer.

EXAMPLE 4

Preparation of
2-Hydroxy-4-Alkoxy-5-Methylolbenzophenone Itaconate Half-Ester

The procedure of Example 2 is repeated with itaconate anhydride to provide the desired monomer.

EXAMPLE 5

Preparation of Copolymers

The monomer of Example 1 is copolymerized with styrene under emulsion polymerization conditions to provide a useful copolymer having enhanced, built-in ultraviolet light stability.

The following materials are used.

| No. | Ingredient | Amount (g.) |
|---|---|---|
| 1 | Distilled water | 322.0 |
| 2 | Siponate DS-10 - Surfactant | 6.0 |
| 3 | Styrene | 47.66 |
| 4 | 2-Hydroxy, alkoxy, methylolbenzophenone maleate half-ester | 8.1 |
| 5 | Ammonium persulfate (in 10.0 g. distilled water) | 1.5 |
| 6 | Styrene | 181.2 |

Ingredient No. 2 is dissolved in No. 1 and the solution is charged into a 1 l. kettle. Then No. 4 in No. 3 is added with stirring. The contents are alternatively evacuated and purged with N$_2$ three times. Then the contents are heated to 75° C. while stirring is continued. At 75° C., No. 5 is added; then No. 6 is charged during a period of 1 hour. The reaction mixture then is held at 75° ±2° C. for 4½ hours, cooled to room temperature and discharged. The resulting latex is coagulated and the copolymer obtained is purified by exhaustive extraction with acetone using a Soxhlet extractor. The presence of the comonomer as a part of the polymer is identified by ultraviolet spectroscopy.

Stability of the copolymer to ultraviolet light is determined by comparing films of the copolymer with films of polystyrene, the latter being synthesized in a similar manner as the copolymer but without using comonomer No. 4. A standard Weatherometer test for 100 hours is used (carbon arc, 40° dry). The test results show that the polymer containing the comonomer changes only very slightly in appearance whereas the polystyrene is noticeably yellowed.

EXAMPLE 6

The monomer of Example 1 is copolymerized with styrene and butadiene under emulsion polymerization conditions to provide another useful copolymer which also has enhanced, built-in ultraviolet light stability. The following materials are used:

| No. | Ingredient | Amount (g.) |
| --- | --- | --- |
| 1 | Distilled water | 935.1 |
| 2 | Kemplex - 100 (42%) | 2.2 |
| 3 | Monawet MB - 45 (45%) | 10.66 |
| 4 | Seed latex (42%) | 57.10 |
| 5 | 2-Hydroxy,alkoxy,methylolbenzophenone maleate half-ester | 24.30 |
| 6 | Itaconic acid | 18.0 |
| 7 | Distilled water | 50.0 |
| 8 | Ammonium persulfate | 2.4 |
| 9 | Styrene | 684.0 |
| 10 | Butadiene | 480.0 |
| 11 | t-Dodecyl mercaptan | 4.8 |
| 12 | Distilled water | 200.0 |
| 13 | Sodium hydroxide (20%) | 18.0 |
| 14 | Ammonium persulfate | 6.0 |
| 15 | Monawet MB-45 (45%) | 21.3 |

Ingredient Nos. 1 through 6 are changed at room temperature into a 1-gallon pressure reactor, and alternately evacuated and purged with $N_2$ three times while agitating at 300 rpm. Then the temperature of the contents is raised to 180° F., and the solution of No. 8 in No. 7 is added. Then Nos. 9 through 11 and Nos. 12 through 15 are added separately and continuously to the reactor during a period of 4 hours. After the addition has been completed, the temperature is increased to 190° F. and the contents are held at this temperature for 2 hours. The reaction mass then is cooled and discharged.

This reaction product also is tested for ultraviolet light stability in a standard Weatherometer test. Accordingly, films are cast from the latex prepared above with and without the comonomer, No. 5. The polymer prepared above, with the comonomer present integrally therein, was far superior with respect to yellowing than the latex without the comonomer.

What is claimed is:

1. Copolymerizable ultraviolet light absorber monomers which are $\alpha,\beta$-unsaturated dicarboxylic acid half-esters of 2-hydroxy,alkoxymethylolbenzophenone, having the formula:

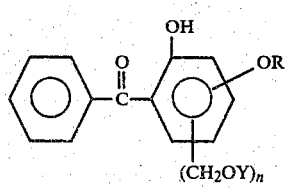

where R is alkyl $C_1$-$C_8$,
n is 1 or 2, and
Y is a half-acyl radical derived from maleic or itaconic acids.

2. An $\alpha,\beta$-unsaturated dicarboxylic acid half-ester of 2-hydroxy-4-alkoxy-5-methylolbenzophenone according to claim 1, having the formula:

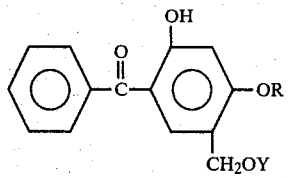

where R and Y are as defined in claim 1.

3. An $\alpha,\beta$-unsaturated dicarboxylic acid half-ester of 2-hydroxy-3-methylol-4-alkoxybenzophenone according to claim 1, having the formula:

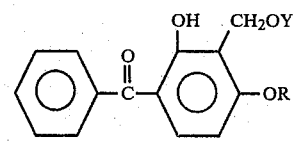

where R and Y are as defined in claim 1.

4. An $\alpha,\beta$-unsaturated dicarboxylic acid half-ester of 2-hydroxy-3,5-dimethylol-4-alkoxybenzophenone, having the formula:

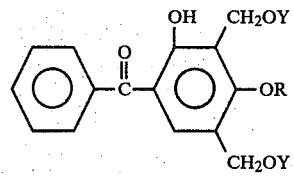

where R and Y are as defined in claim 1.

5. A monomer according to any of claims 1-4 in which R is $C_1$-$C_3$.

6. A monomer according to claim 2 which is 2-hydroxy-4-methoxy-5-methylolbenzophenone maleate half-ester.

7. A monomer according to claim 3 which is 2-hydroxy-3-methylol-4-methoxybenzophenone maleate half-ester.

8. A monomer according to claim 4 which is 2-hydroxy-3,5-dimethylol-4-methoxybenzophenone maleate half-ester.

9. A monomer composition comprising a mixture of the monomers having the formulas

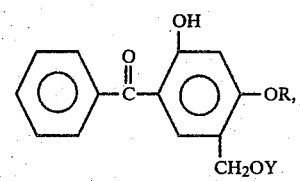

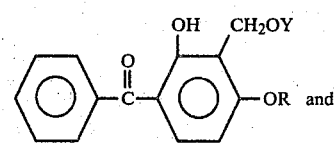

-continued

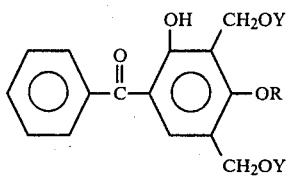

where R is alkyl $C_1-C_8$, and

Y is a half-acyl radical derived from maleic or itaconic acids.

10. A monomer composition according to claim 9 which is comprised essentially of the monomers having the formulas

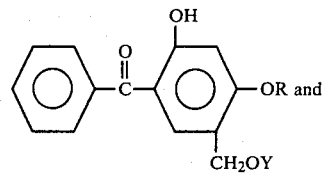

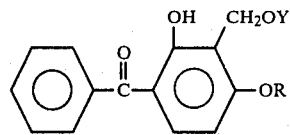

where R is alkyl $C_1-C_8$, and
Y is a half-acyl radical derived from maleic or itaconic acids.

11. A monomer composition according to claim 10 in which said monomers are present in a ratio of about 3:2.

* * * * *